United States Patent [19]
Dahlquist

[11] Patent Number: 6,027,464
[45] Date of Patent: Feb. 22, 2000

[54] SLEEPING AND THERAPY SYSTEM WITH A PERSON HYDRAULICALLY SUPPORTED BY IMMERSION IN WATER

[76] Inventor: Daryl Leroy Dahlquist, 15250 SE. 272nd St., Kent, Wash. 98042

[21] Appl. No.: 08/778,547

[22] Filed: Jan. 3, 1997

Related U.S. Application Data

[60] Provisional application No. 60/014,352, Mar. 28, 1996.

[51] Int. Cl.$^7$ ..................................................... A61H 7/00
[52] U.S. Cl. ........................... 601/148; 601/151; 601/158; 601/160
[58] Field of Search ..................................... 601/148, 149, 601/150, 151, 152, 158–160; 128/202.12, 205.26; 600/21; 4/528, 533, 534, 585

[56] References Cited

U.S. PATENT DOCUMENTS

| | | | |
|---|---|---|---|
| 2,516,419 | 7/1950 | Reyniers | 600/21 |
| 3,355,230 | 11/1967 | Trexler | 600/21 |
| 3,977,396 | 8/1976 | Cartier | 601/151 |
| 4,509,513 | 4/1985 | Lasley | 128/202.12 |
| 4,635,620 | 1/1987 | Ricchio | 601/148 |
| 4,648,392 | 3/1987 | Cartier et al. | 601/151 |
| 4,925,133 | 5/1990 | Wurst et al. | 244/118.5 |
| 5,309,901 | 5/1994 | Beaussant | 128/202.12 |
| 5,437,602 | 8/1995 | Polyakov et al. | 600/21 |
| 5,477,850 | 12/1995 | Zegler et al. | 128/205.26 |
| 5,672,148 | 9/1997 | Maunier | 601/148 |

FOREIGN PATENT DOCUMENTS

| | | | |
|---|---|---|---|
| 2639538 | 6/1990 | France | 601/148 |
| 1915636 | 10/1970 | Germany | 601/151 |
| 1695918 | 12/1991 | U.S.S.R. | 601/151 |
| 1180234 | 2/1970 | United Kingdom | 601/151 |

*Primary Examiner*—Richard J. Apley
*Assistant Examiner*—Benjamin K. Koo

[57] ABSTRACT

Apparatus and method for sleeping, resting, or receiving therapy while immersed in water. The buoyancy forces eliminate concentrated support forces on the body, relieving back and neck stress, decubis ulcers, bed sores, and the like. The person is contained within a waterproof suit and substantially immersed in warmed water. Suit ventilation means and safety monitoring instrumentation are disclosed. Therapeutic gasses and vapors may be wholly or selectively applied to the body while sleeping or resting. Salves and the like may be applied remotely and specifically through tubes. The system also has provision for applying traction and manipulation therapies. The system is adaptable for veterinary use.

20 Claims, 5 Drawing Sheets

SLEEPING AND THERAPY SYSTEM WITH A PERSON HYDRAULICALLY SUPPORTED BY IMMERSION IN WATER

CROSS REFERENCE TO RELATED APPLICATIONS

The present application claims benefit of filing date of co-pending Provisional Application # 60/014,352, Sleeping System With A Person Hydraulically Supported by Immersion In Water, filed on Mar. 28, 1996.

BACKGROUND OF INVENTION

1. Field of Invention

The field of the invention is anti-gravity resting or sleeping systems. Anti-gravity condition is achieved by substantial immersion in a liquid. The system supports the body with evenly distributed support forces of hydraulic origin. Such a system is useful for providing rest for persons with chronic back problems, obesity, invalids, relief of stress on surgical and trauma wounds, the prevention or treatment of decubis ulcers (bed sores), and other conditions aggravated by the forces of gravity. Colostomy, catheterized, paraplegic, and unconscious patients can use the sleep system. Traction forces may be applied to the body. The system also permits the application of therapeutic gasses and vapors to all or part of the body.

The invention may be modified for veterinary use, particularly with large animals. It is apparent that for veterinary use, the present invention need only be modified to suit the specific anatomy of the animal.

2. Description of the Prior Art

Prior art related to sleeping or resting with hydraulic support rely on utilizing a liquid or air filled mattress upon which the sleeper lies.

Support forces in waterbeds are more evenly distributed over the body than in conventional fiber or foam filled or spring mattresses, but still have considerable variation in support pressure which can cause bed sores in immobile patients. Horizontal support beds all apply various stressing forces to the spine and neck and have pressure points on various parts of the body. Related art in the field of hydraulic massage have the person awake and immersed directly in water. Long periods of direct immersion are not practical for well known reasons. U.S. Pat. No. 4,925,133 by Steven Wurst, et al, prior art in anti-gravity suits, discloses a water-containing suit for hydraulically supporting the operator of a vehicle such as an airplane during high G maneuvers. Such a suit is not suitable for sleeping.

The application of therapeutic gasses is usually done by taping an air tight covering or bag onto a limb or to the body. Large areas are treated even though only a small area requires treatment. U.S. Pat. No. 5,437,602 by Polyakov, et al. discloses a limb treatment bag and describes difficulties dispersing the gas, avoiding humidity build-up and constriction problems encountered using bag taped onto a limb. Gas therapy with the prior art is necessarily applied for a relatively short time which in turn encourages use of higher than necessary, possibly caustic or detrimental, concentrations of the gas. In addition, tape adhesives cause mechanical discomfort, skin breathing problems, reactions to adhesives, and clean-up labor after use.

The present invention overcomes the limitations of prior art both as a sleeping system and as a gas therapy chamber. Body support forces are minimized and distributed, and gas therapy can be applied wholly or locally as will be shown.

SUMMARY OF THE INVENTION

In the present invention, the rester, sleeper, comatose person, or person receiving therapy of various types is inside a water tight envelope or suit suspended in a tank or pool of water. At least one layer of permeable material is between the sleeper and the water tight envelope to absorb moisture and to provide passages for moisture clearing air to follow. The permeable material provides thermal insulation between the water and the person and in co-operation with air forced through the permeable layer, permits the body's own temperature regulation system to function naturally.

Air from a compressor and flow regulating means is introduced into various parts of the suit, especially at the hands and feet, through tubes. Air flows through the permeable layer expelling air contaminated or fouled by, skin exudations (primarily perspiration) and other sources expelling them through the neck of the suit.

The permeable layer, being substantially hollow and air-filled, provides considerable buoyancy. Compensating weights are distributed over the suit to approximately neutralize buoyant forces. The resting position of the sleeper may be adjusted from floating horizontally to vertical by the anti-buoyancy compensation weights or by weights resting on the bottom of the tank and attached to the suit by strings. Sinker weight in excess of that required to overcome buoyancy provides gentle traction forces to the spine. It should be noted here that the vascular system will see negligible difference between vertical and horizontal. Since water pressure is on the outside of the suit and the suit and permeable layer are flexible, the water pressure forces are transferred to the skin. The skin of a person or animal is designed to withstand hydraulic forces of this magnitude, but in the natural state, the forces are from within the body. The body is held in its form largely by the strength and shape of its skin. This is especially true for those parts only attached loosely to the skeleton such as soft tissue. Since skin is somewhat elastic, as are blood veins, veins near the skin are under internal pressure and can fail to the condition known as varicose veins. With the external pressure via the suit, this stress is alleviated and pooling of blood and lymph is discouraged. The skeleton is heavy bone and in all cases will tend to settle by gravity, causing some stress on the surrounding tissue. However, since that tissue is supported nearby by the suit, the forces are distributed optimally, and is smaller than in conventional sleeping systems.

Traction and compression forces can be applied to any portion of the body, in particular to the spinal column. Forces may localized and customized between a point of suspension and another point to which weights are attached. Limb traction and/or extension to stretch joint structure, muscle, or ligament tissue may applied in a similar manner.

The invention provides for manipulation of limbs and various portions of the body by water movement from jets and or moving limbs by means of cords co-operating with means to provide mechanical motion. The body is moved in the manner of a string operated marionette.

Various instrumentation for monitoring the condition of the sleeper and for monitoring the integrity of the system itself are desired, but not mandatory in all applications. Suit leaking, water temperature, and depth of immersion of the suit are typical for system monitoring. For monitoring the sleeper, skin temperature and moisture, respiration, heart rate, electrocardiograph, muscle activity, and the like are non-invasive and simple enough to be used in non-clinical settings. In most cases, the inherent pressure of the suit system against the skin will be adequate to hold the transducers in place without taping. Transducers for all of the above monitoring are readily available with instructions for their use in terms any mechanic should comprehend.

It is possible to use the air system to medicate the sleeper with various transdermal or surface active medicament prescribed for the sleeper. Since the number and placement of the air inlets is optional, air may be applied in the vicinity of, or directly onto a decubitus ulcer, infection, wound, burn, or area needing special attention, moistening, drying, or medication. Extra oxygen, ozone, moisture, aerosols, antibiotics, or oil are possible medicament. Salves, liquid, and transdermal medicaments can be precisely placed by sending them through tubes similar to the air tubes directly to the required point on the body. Furthermore, it is possible to reverse the flow and draw out air to prevent the general spread of medicaments, suppuration gasses, or to take air or fluid samples when conditions warrant.

The distributed, low support pressures combined with ventilation and means to apply therapeutic materials, make the hydraulic sleep system ideal for relief and treatment of severe burn victims.

Because there is no bed surface, the body can be manipulated through most natural movements to provide movement stimulation to the limbs and spine hydraulically or by systems of strings and pulleys.

Jet and bubble massage features may be incorporated into the system. Their specific applications and means are well known in the art.

For the purposes of this disclosure and claims, resting, sleeping, and receiving therapy are synonymous activities. The use of the invention is not dependent on the user's state of consciousness or purpose for being in the inventive apparatus. The word animal includes people, and for the purpose of this disclosure and claims, the word person is to be construed with an expanded definition to include domestic, farm, and other animals under care or treatment by people.

Accordingly, it is an object of the invention to provide a sleeping system wherein the gravity resisting forces supporting a sleeping person be distributed substantially over the entire body, eliminating pressure points and attendant trauma from restricted blood flow and to reduce or eliminate stresses on the spine.

It is another object of the invention to deliver medication or other attention to the skin, either generally or specifically.

It is another object of the invention to provide a massage to the body surface.

It is another object of the invention to provide manipulation to the body or parts of the body.

It is another object of the invention to monitor the physiology of the body for safety, diagnostic, or research purposes.

It is another object of the invention to provide traction either generally or specifically to various parts of the body.

DETAILED DESCRIPTION OF THE PREFERRED EMBODIMENTS

The hydraulic resting, which encompasses sleeping, apparatus or system disclosed herein is has person substantially immersed in a liquid and protected from the detrimental effects of that liquid by being separated from the liquid by means of a liquid-proof membrane fashioned into the form of a container, suit, or envelope completely encasing the submerged portions of the sleeper. The liquid is usually pure water or water containing an appropriate type and quantity of disinfectant. Various well known salts may be dissolved in the water to increase the specific gravity and/or provide a bacteriostatic property. The liquid may be a gel, slurry, or foam when specific gravity or viscosity substantially differing from water or salt solutions is desired.

Figures 1, 2:
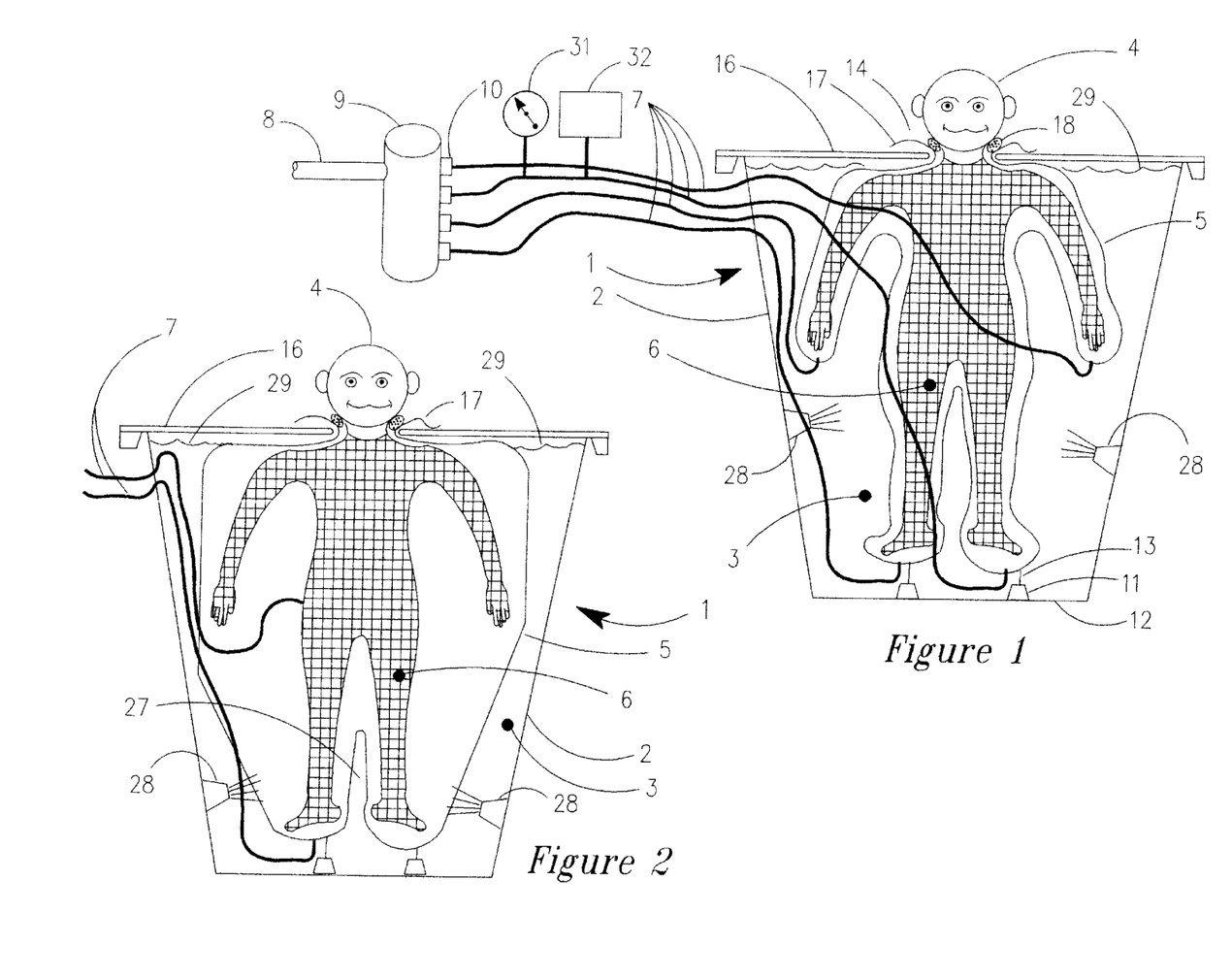
FIG. 1 is a cut-away view of the sleep system utilizing neck support and a water tight suit approximately conforming to a human figure.
FIG. 2 is a cut-away view of the sleep system utilizing neck support and a water tight envelope.

Referring to FIGS. 1 and 2, the resting and sleep system 1, consists of a tank 2 filled with water 3 which is held at a constant temperature within approximately a 2 degree range between approximately 70 F. and 85 F. degrees. Cooler water can be tolerated by the use of more insulation described later. For healthy people, in no case should the water temperature exceed 95 F. The system may be used in life support applications where external heating or cooling is required to maintain normal body temperature. The parameters of application will have to be medically tailored for the individual case.

The person 4 using the system is encased in a waterproof suit or envelope 5. A layer of flexible air-permeable, water wicking material 6 is between the person and the waterproof suit as insulation, to absorb perspiration and to provide passage for clearing air. The permeable material contains a labyrinth of interconnected passages communicating from side to side and from edge to edge in all directions so that air may flow through the material in any direction, especially the long way, parallel to the sides. Appropriate materials are well known in the garment industry, particularly for sport garments, outdoor garments, and underwear. Flannel, fleece, woven fabrics knits, felts, "jogging suit", "sweatshirt", and blanket fabrics are examples. Cotton or non-itching wool are the preferred natural fibers. Fabrics of man-made fibers and blends are not excluded.

Joining methods used to fabricate larger permeable structures must also be permeable. Sewing is preferred.

The drawings show the permeable layer as a body suit of the Union Suit or Jogging suit style plus hand and feet coverings. It is equally useful to fashion the permeable layer more closely fitted to or attached to the waterproof suit or bag as a liner.

Since the whole suit is pressed against the body by hydrostatic pressure, a second inside layer (not illustrated) fashioned from a slippery fabric such as nylon tricot can be used to ease the effort required to move within the waterproof envelope of FIG. 2 or when the arms are not in the arm tubes of FIG. 1. The slippery fabric is best used in the form of pajamas.

The envelope, or suit, 5 is constructed of water proof sheet material. Many materials are satisfactory and known in the tent, rainwear, outdoor sport, and foul weather clothing, and construction industries. The preferred material is poly-vinyl sheeting 0.002 to 0.01 inches thick.

The waterproof suit may be constructed in one piece, or a plurality of pieces, joined and sealed by any, or combination of, common techniques such as welding or gluing. To ease getting into or to customize the suit, any of several temporary or site-applied sealings such as tape, glues, clamps, or waterproof zipper like devices may be employed. The seals are subject to hydraulic pressure tending to keep them closed. There is never any internal pressure tending to separate the seals. The structural demands on any sealing method is small and will tolerate weak sealing methods. Movements of the sleeper are the largest hazard causing accidental unsealing. The preferred zipper device is inter-digitated ridges on mating tape-like strips which are then attached to the suit surfaces. The zip-seals on re-closable sandwich bags are examples of a suitable zipper.

Ultimately, perspiration absorbed by the permeable layer will raise the relative humidity within the envelope enough to interfere with evaporative cooling and/or condense on the inside of the waterproof envelope. To prevent moisture accumulation, air is passed through the permeable fabric at a volume of 1 to 5 cubic feet per hour. The air may be monitored for vapor content and the volume controlled accordingly to keep the relative humidity at about 50%. Although it is not necessary to do so to practice the invention.

It is desirable to have air flow over the whole body. Thus, at minimum, the air supplied by tubes 7 should enter near both hands and feet. Extra air entering at the torso reduces the net volume required at the feet, thus, reducing the tendency to over-cool the legs. FIG. 1 shows the tubes disposed externally to the suit. There is no functional difference whether the tubes are inside or outside the suit, or constructed as an integral part of the suit itself. Air channels constructed as part of the suit using the soft material of the suit will be collapsed by the water pressure unless overcome by the pressure of the air supply. The maximum pressure required is a head of approximately 5 feet of water ie, 2.2 psig.

FIG. 2 shows one of the tubes 7 terminating at the body instead of the edge of the suit. Air must be injected as close as possible to the permeable layer to prevent it being pinched by the flattened portions of the suit or envelope. Air will still flow, but it will be bubble like and generally flow upward following the path of least resistance between the waterproof layers.

Clean warmed air is supplied by a compressor through tube 8 to plenum 9 at 2.5 to 10psig. Higher plenum pressures will not defeat the operation of the invention, but cause unnecessary complications like higher energy usage, expansion cooling at the flow regulators, noise, etc for no useful purpose. Flow into tubes 7 is individually controlled at tube connection ports 10. Tube ports 10 comprise conventional components including a shut off valve, tube attachment bib, and flow regulating means such as needle valves, orifices, nozzles, or small bore tube with length several times the inside diameter.

The theoretical flow formulas for orifices, nozzles and small bore tubes are available in most handbooks dealing with pneumatic control. The approximate formula for air through orifices and nozzles is:

$$\text{Cubic feet/hour} = 2.1 * \text{square inches} * (\sqrt{0.072 * \text{psig}})$$

Figures 6, 7:
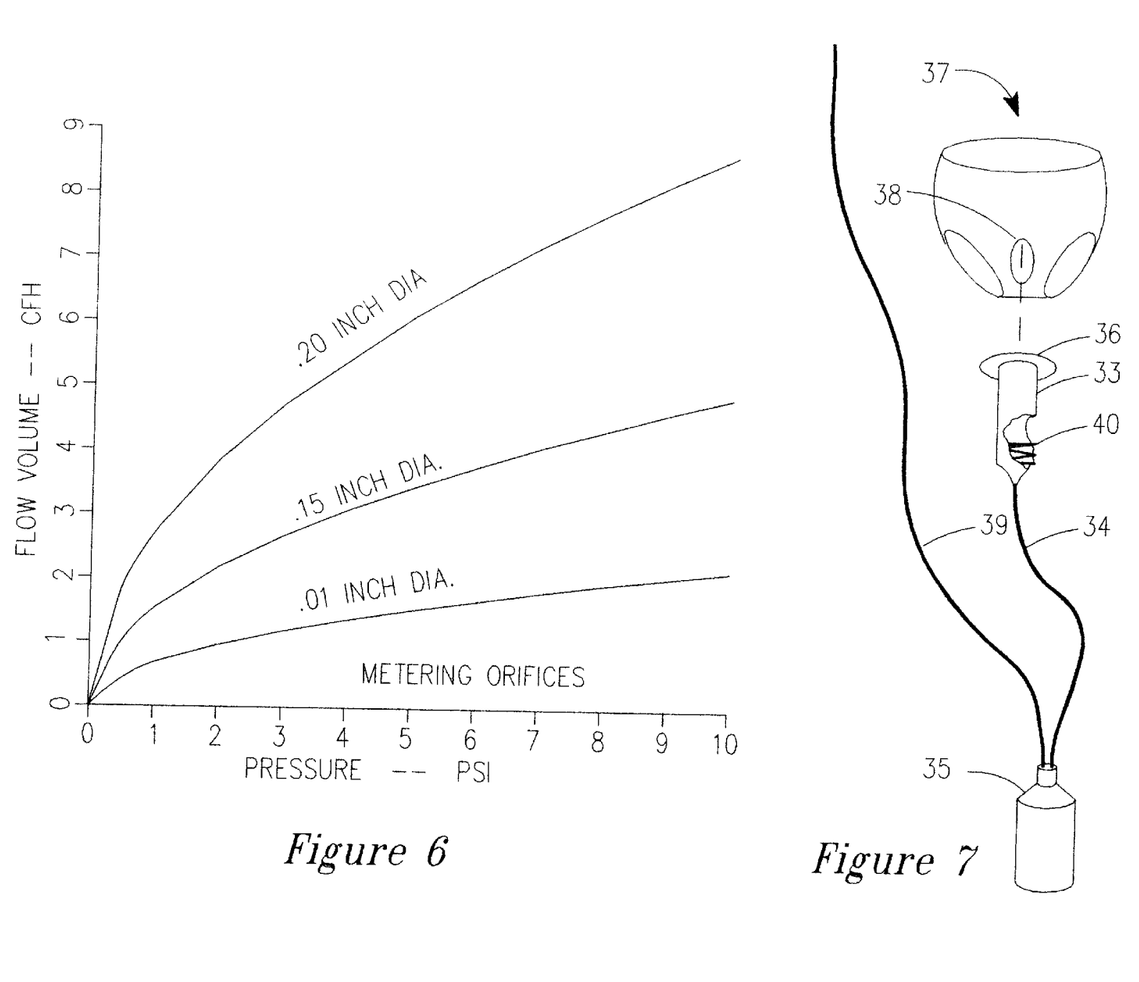
FIG. 6 is a graph depicting the operation of orifices of various sizes.
FIG. 7 is an embodiment of a urinal system for use within the present invention.

FIG. 6 is the graphical solution for the above equation.

Small bore tubes having lengths several times the diameter have the have similar characteristics to orifices and nozzles until the flow exceeds a particular velocity, ie Reynolds number greater than about 2000, from that point, the flow is relatively constant despite changing supply or discharge pressure.

The formula is theoretical, based on several assumptions, and is affected by many factors introduced in the manufacture of the air system as a whole. Some experimentation is necessary to produce an orifice, nozzle, or tube that has the desired flow. Obviously, needle valves are adjustable by inherent design and the knobs can be marked with a pre-calibrated scale.

Flow meters may be installed in the tubes but are needed only to calibrate the original set-up. In general for healthy users, the user generally does not have to know or adjust the flow. One time factory adjustment by selecting a calibrated orifice or Reynolds tube is adequate.

Some users will require adjustment of the parameters. The conditions and reasons when adjustment is needed are given elsewhere in this specification.

Many flow meters for low volume air flow are available in commerce. Two of the simplest and most reliable are the ball in a tapered tube design and propellers or paddle wheels which rotate in response to the flow of air past the rotor.

The static (no air flow) pressure is atmospheric pressure (0 psig) everywhere within the suit. The pressure at the delivery end of the supply tube will be 0 psig plus whatever pressure is required to force the air through the weave of the permeable fabric layer. The pressure will never exceed the water head pressure at the point of entrance into the suit because if flow through the permeable layer is restricted sufficiently to create that much back pressure, the suit will tend to slightly expand like a balloon and release any pressurized air around the fabric.

The space taken up by the permeable layer is mostly hollow and provides considerable buoyancy causing the encased sleeper to float. Therefore, compensating weights (not illustrated) located at intervals of about 1 foot or less are distributed over the suit to cancel out buoyancy approximately evenly over all parts of the body. The weights are in pockets on the suit, attached by tape or clamps, or hooked into grommeted holes. Clamps are preferred for their versatility and ease to use. Clamps like electrical alligator clamps and others styles having teeth or sharp points should not be used. Clothes pins and paper holding clamps are satisfactory. A clamp called a bulldog clamp made of flat spring steel in various sizes and available in stationery and art supply stores is suitable. The operating handles on the bulldog clamps are wire loops ideal for attaching weights.

The compensating weight is the weight of water corresponding to the volume of air entrapped in the permeable layer associated with each weight holder.

The essential principal for buoyancy is that the buoyant force is the weight of water displaced by the submerged article. In this case, an animal weighs approximately the same as the water displaced. Thus, the additional buoyancy is supplied primarily by the additional space occupied by the permeable layer. For initial compensation, only the permeable layer has to be considered. Since fat weighs less than water, bone weigh more, and muscle and blood about the same, small adjustment will be necessary for each sleeper.

The formulas for calculating the approximate weight in ounces to put into a pocket or attach to a body zone is:

Weight of displaced water=Average circumference of body section of interest)*(thickness of permeable layer)*(distance between adjacent weights)*0.58

Submerged weight of sinker=Weight of displaced water.

Out of water weight of sinker=(Submerged weight of sinker)*(SG+1)*0.58

Dimensions in inches and ounces. SG is the specific gravity of the weight material. SG=11.34 for lead. SG=7.87 for iron.

The specific gravity of other materials is readily found in materials handbooks or may is easily measured without sophisticated tools. Note that the density of a material expressed in the CGS (metric) system is numerically same as the SG.

One or more sinkers totaling the calculated weight are attached to the suit within the zone of interest. More or less weight is added to compensate for specific gravity variations in the body of the sleeper and the volume and SG of the fibers of the permeable layer.

When in doubt of the amount or placement of the weights, simple experiments with variations of amount and placement of the weights is in order and well within the capabilities of the ordinarily skilled mechanic.

A means to hold the sleeper's body in the most comfortable position is provided. In most cases the preferred position is approximately vertical. Restraining straps and/or excess sinkers will work. The preferred means is by weights 11 resting on the bottom of the tank 12 and attached to the suit by straps or cords 13 of suitable length. The amount of weight required will be only a few ounces as the sleep suit has been adjusted to be near neutral buoyancy. Movement of the body can lift and reposition these weights easily.

To prevent the sleeper from slipping under the water and drowning or flooding the suit by submerging the neck opening, his head and the neck of the suit are held above the water by mechanical means. FIGS. 1, 2, 4, and 5 illustrate a neck stock providing support. The neck of the sleeper is put through an opening 14 in tub lid 16, which is split 15 to gain access. The suit neck 17 also passes through the opening, terminating outside the tub and removably attached to the lid by taping or clamping to prevent accidental withdrawal of the suit neck into the water. Padding 18 is placed around the neck for comfort. The sinker weights are adjusted so that the lid comfortably supports un-buoyed weight by the neck and chin. Padding 18 is relieved under the ears to reduce or eliminate pressure on the carotid arteries.

FIGS. 1 and 2 show the lid 16 as a hard surface like a table top. Alternatively, a canvas like cover is equivalent.

It is to be appreciated that the primary purpose of the lid is to hold the head of the sleeper above water. Therefore, the term lid can refer to a trestle, girder, beam, or the like to carry the neck stock or other supporting means.

Figures 4, 5:
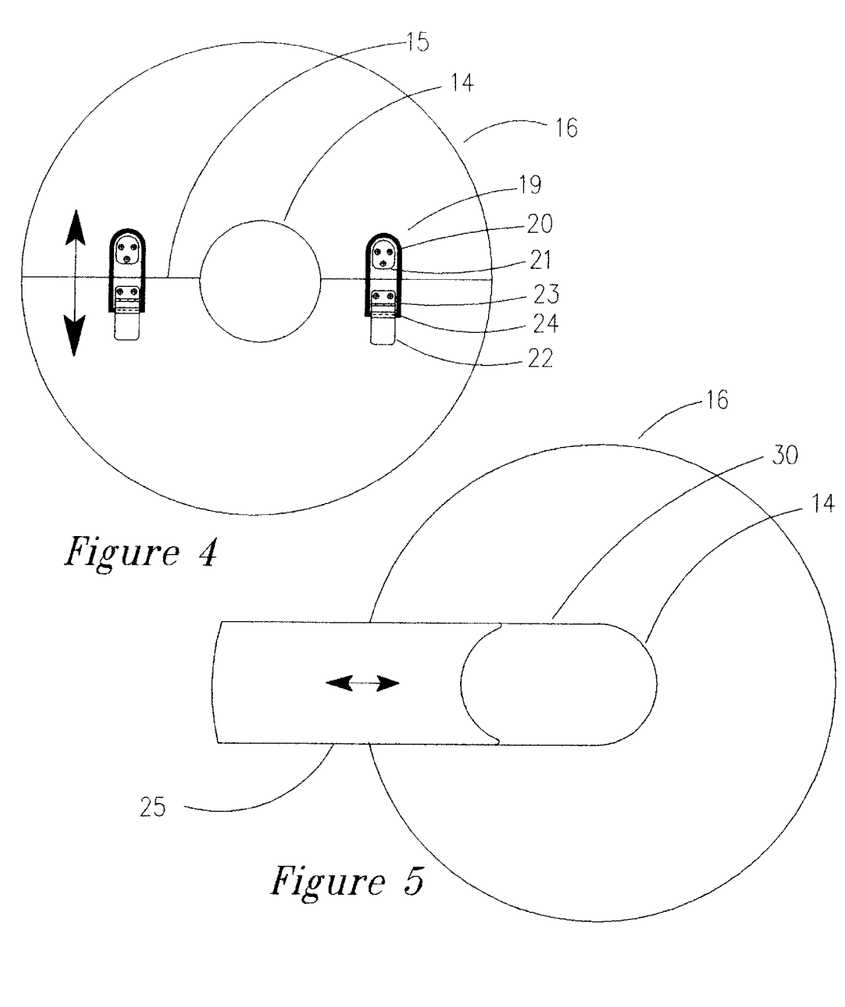
FIG. 4 is a plan view of the split lid support means.
FIG. 5 is a plan view of an alternate slide closing support means.

Refer to FIG. 4. The rigid stock illustrated is split in at least two pieces like a table top to provide entry into the neck hole. The halves are then closed and latched with common latching hardware 19 such as used for tables, windows, tool boxes, and lunch boxes. Preferably, the latch release is accessible from both sides. The latch shown in FIG. 4 is of the loop 20, bollard 21, toggle link 22 type used on tool boxes. Hinge 23 and loop pivot 24 are necessary parts of the toggle link.

The stock may be fitted with hand or arm passage holes (not illustrated) to permit the hands to be raised to the head to adjust the cushions or other activities such as scratching the nose.

It is obvious that other opening means such as a slot open to one side of the table cooperating with a slot filling piece perform exactly the same function as a split table. FIG. 5 illustrates a lid 16 having a slot 30 and a slidable or removable opening 25 to gain access to the neck hole 14. The slidable closure 25 may slide on simple tracks and be secured by latches previously described.

Alternatively, hammocks, pallets, or chaise lounge type devices may be used in the water tank in a similar manner to their dry use, except that there is negligible weight to support. Weighted belts or some other means to provide hold down forces and the safety harness 26 are recommended.

The waterproof bag or envelope illustrated in FIG. 2 works exactly like the suit of FIG. 1 except that the arms are within the general envelope. This embodiments makes best use of an optional inserted blanket type permeable layer (not illustrated) and of a slippery pair of pajamas. Gloves and socks are not needed with a blanket liner.

FIG. 2 shows a slit 27 between the legs of person within the envelope, forming penguin feet to allow some mobility out of the tank. A flexible boot, shoe, or slipper, (not shown in FIG. 2), of rubber like material, similar to an Aqua-Sock Shoe, having inherent stability or a strap to tighten for stability, may be worn to prevent slipping while entering or leaving the tank. In most cases, a treaded sole 42 is included. The shoe does not need to maintained with a dry interior.

Figure 3:
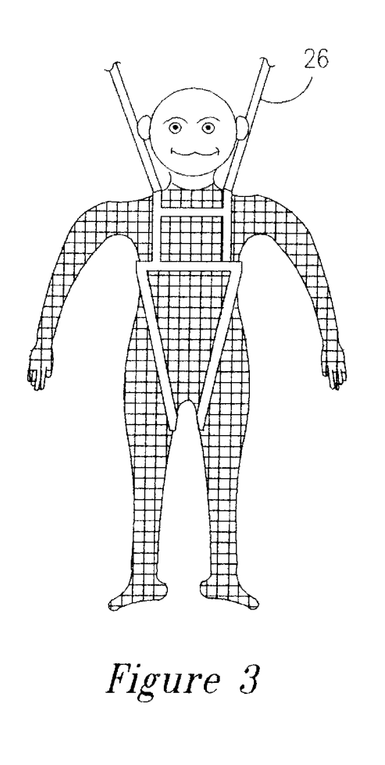
FIG. 3 shows an optional harness support for the sleep system.

FIG. 3 illustrates a harness 26. The primary purpose for the harness is for lifting the user, particularly an invalid, from the water. However, its use as a safety device or to provide psychological comfort to the user is not to be overlooked. Suitable harnesses are readily available as parachute harnesses or safety harnesses used by construction workers and others. Most industrial tool and safety supply stores have several sources cataloged.

The harness may be used in conjunction with the neck stock or alone to provide support for keeping the sleeper's head above the water. When used with the neck stock, it is either attached to the underside of the lid or the lifting straps pass through openings in the lid and are attached to an overhead crane or trestle (not illustrated). During immersion, the weight supported by the harness is negligible. When a head lift is used, the harness is primarily for security and for lifting the person out of the water.

When the harness is used alone, the open end of the envelope is supported above the water surface by hangers usually attached to the harness straps or the supporting crane or trestle.

Figure 9:
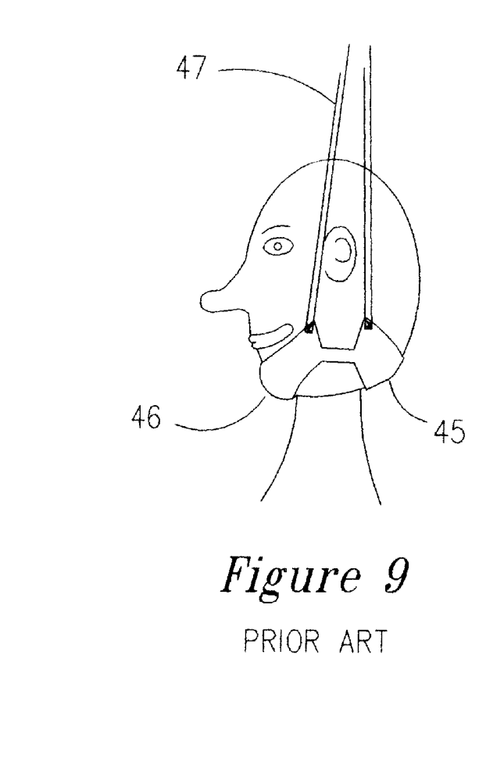
FIG. 9 is a view of a prior art head supporting system.

Head restraints to be used with the harness are not shown, but consist of strapping or netting attached to the lifting straps or separately supported. Head restraints or supporters are used when the harness is used without the neck stock. FIG. 9 shows a commercially available variety having neck 45 and chin 46 straps connected to lifting straps 47 for supporting the head are available from hospital and sickroom suppliers. These are usually cataloged as head halters for applying cervical traction. A head halter may be used as the head restraint or as the sole or primary means to keep the head above the water.

By adjusting the buoyancy of the submerged portion of the sleeper, the tension on the neck is controlled thus providing traction forces on the neck portion of the spinal column. Similarly, by attaching weights, flotation, or mechanical support to various parts of the body, all or selected portions of the spine or other body parts may be put into traction tension or compression as required for the benefit of the patient or sleeper.

The foregoing embodiments all presume that the body is submerged no deeper than the chin, with the head supported above the surface of the water. However, complete submersion is possible and, when psychological resistance to submersion is overcome, practical and useful. With complete submersion, the head is not supported artificially, but by buoyancy as is the rest of the body. The means enabling the head to be submerged is the addition of means for un-obstructed breathing. Two means for providing breathing air are disclosed. They may be used individually or together. The open end of the water tight envelope is supported above the water surface as before.

Figure 10:
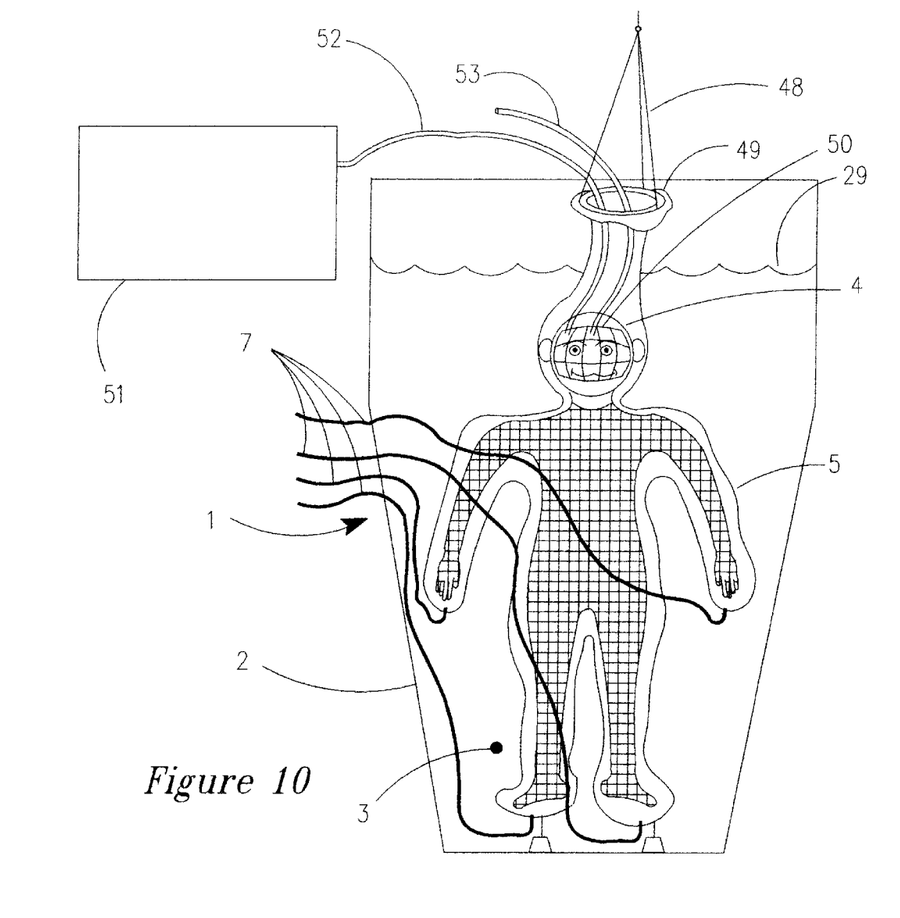
FIG. 10 is a partial cut away showing the sleeper totally immersed within the supporting liquid.

FIG. 10 illustrates the sleeper in the completely submerged embodiment. The sleeper may be completely submerged as shown or held above the water as much as desired. This method of support is less confining and evokes different psychology from the neck stock embodiment.

The envelope 5 continues around and above the head 4, terminating above the water line 29 at an attachment point for support cords 48 extending from a trestle or other support means (not illustrated). FIG. 10 shows the envelope secured to a ring 49 which distributes the supported weight over a larger cross section of the envelope and to which the support cords attach. Any means of attachment that can safely support the expected weight will suffice. The safety harnesses previously described may be included in the apparatus.

A frame 50 about the face to hold the water tight envelope away from the nose and mouth comprising of a shield similar to the face guards common in athletic supplies is one. The face mask use by baseball catchers or the helmet and face guard of football players are typical. The face frame embodiment also requires that adequate fresh air be supplied to the face area. Since there is no pressure required, fresh breathing air can be supplied by the aforementioned air compressor or a separate high volume, low pressure, source 51 such as a venturi ejector or a fan type compressor through flexible tube 52 to the area of the face.

Tube 53 between the face area and open to atmosphere at the other end is optional, but recommended, to provide a secure path for exhaled air and excess air from the supply. Unless the narrowed neck of the envelope becomes twisted and tightly closed at approximately the waterline air can escape easily through the above head portion even if it is collapsed by the surrounding water. Tubes 52 and 53 must be large enough to pass the normal volume of breathing without noticeable pressure drop. Tube 52 can be as small as ¾ inch inside diameter, and tube 53 should be 1½ inches inside diameter minimum.

The other means to provide breathing air is mask system which may be a breathing machine used for relief of sleep apnea breathing problems. The apnea machine supplies adjustable low pressure air to the sleeper through a mask similar to a gas mask. The apnea machine is designed primary keep the airway open to prevent snoring and consequent choking. In the present invention, its use is also to provide air for breathing. The apnea air supply and tube correspond to illustrated supply 51 and tube 52. The present invention applies continuous hydraulic pressure on the chest during use, and that pressure must be overcome by the muscles and bone resiliency used for normal breathing, the apnea machine can be used to provide internal lung pressure to assist in overcoming the hydraulic pressure on the chest for both healthy sleepers and for those with impaired chest function relating to breathing.

In prior art beds the body regularly moves to relieve aches from bed pressure. In the hydraulic sleep system there is no bed pressure so the body may not be readily prompted to move about. Furthermore, the present invention is ideally suited for persons with mobility problems, paraplegics and the like who often have little or no ability to move some of their limbs under their own power. Two means to move the body or parts of the body are provided.

Jets of water 28 project from the tank walls to provide massage and motion to reduce stiffness from immobility. The jets and the subsequent general motion of the water will gently move the body.

Figure 8:
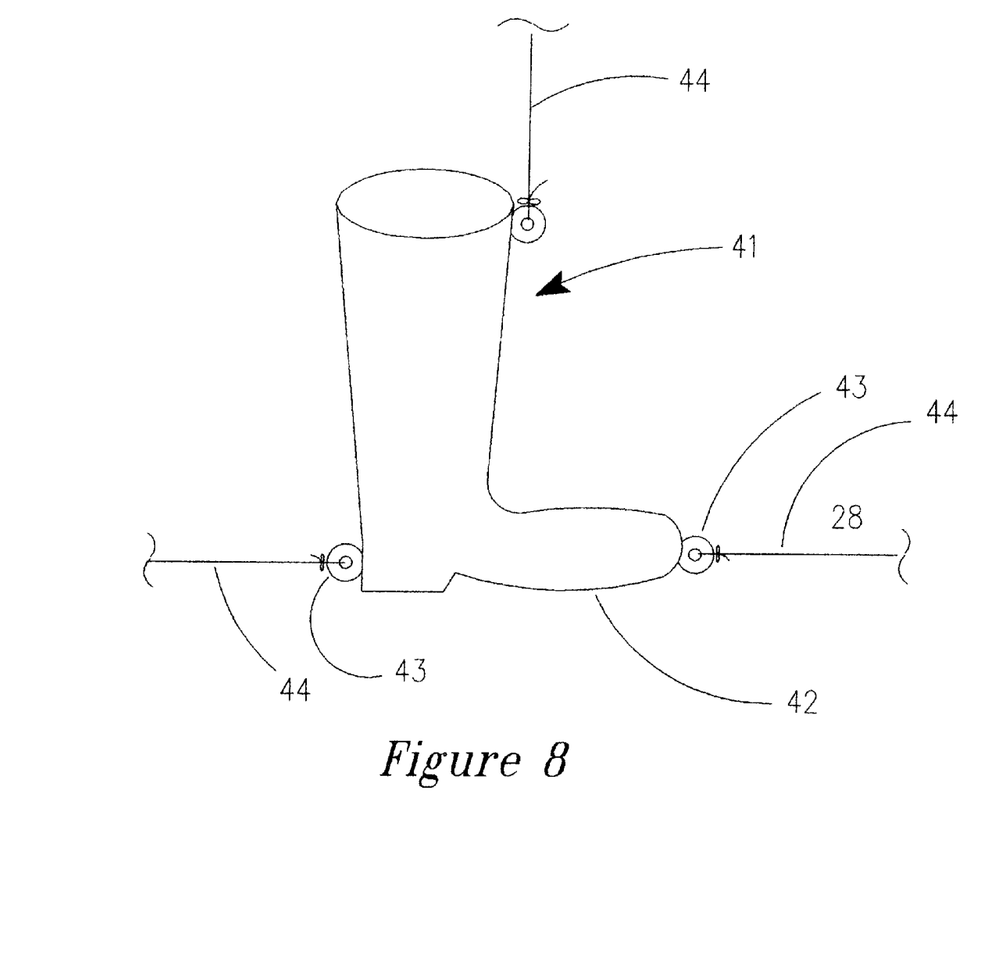
FIG. 8 is a view of a typical boot or shoe for attaching manipulation strings.

FIG. 8 illustrates a Wellington type boot 41 fitted with eyes 43 for attaching cords which may pass through a system of pulleys (not illustrated) and operated by any of several commonly available mechanical motion imparting means (not illustrated), to move the legs in the manner of a string operated marionette. The attachment to a boot is for convenience.

Any method of permitting the string to move whatever part of the body it is attached to is anticipated. Such attachments may be to other garments, straps, or similar devices, or eyes or clamps attached to an effective point on the waterproof envelope, thereby permitting motion to be imparted to a limb or other body part.

Manipulation may be equally provided by other means such as rods in place of the cords.

FIG. 8 illustrates cords 44 for pulling a leg to and fro and lifting the knee. Similar structures are intended to move other parts of the body. In some applications, for some patients, the return force may be provided by weights and/or whatever muscle strength the patient posesses.

A leak causing flooding of the suit does not present a drowning hazard, but does reduce buoyancy, increases the weight supported by the neck, defeats the thermal insulation properties of the permeable layer, and soaks the body in water. A water detecting sensor in the lower part of the suit is a needed safety feature. The wiring for such a detector may be threaded through the air tubes and the detector transducer placed near the ends of the tubes at the feet and hands.

Suitable water detecting transducers are common in the boating and process control industries. A novel flooding monitor can be incorporated by noting the pressure required to keep air flowing into the feet of the suit. The pressure will sharply increase if the permeable layer becomes saturated with water thereby plugging the labyrinth of air passages.

Depth of immersion can be determined by directly measuring pressure at depth or by bubbling air through at least one extra tube open to the water near the lowest portion of the suit. For air to flow, the air pressure must equal the hydraulic head at the tube's open end. Air pressure throughout the tube is constant and directly proportional to the depth of the submerged tube, thereby the depth of the tube end is determined by measuring the air pressure required to cause air to flow through the tube.

Both flooding and depth instruments are implemented simply by attaching pressure gauges or pressure switches at the plenum end of air tubes placed as described above.

FIG. 1 shows a pressure gauge 31 and a pressure sensitive switch 32 to operate an alarm sensing the pressure in one of the foot ventilating tubes. The gauge is redundant when the switch-alarm combination is used.

Skin temperature measurement senses the body's regulation of its temperature within the suit. While low skin temperature does not necessarily indicate imminent danger to the sleeper, it does indicate that the body is attempting to conserve heat by reducing blood supply to the surface. High skin temperature may indicate a lack of ability to remove body heat. It also suggests increased perspiration in the healthy person. Either elevated or low skin temperature suggests a requirement to adjust water temperature or air flow.

Various additions and change of details to improve the comfort, safety, and utility of the invention are permitted. For example, panels may be cut into the suit to provide access to wound dressings, relief, visual examination, etc. The openings may be closed by the above described zippers or tape.

Finally, because the system is often used with sleepers having mobility problems making it difficult to get in and out of the tank or suit, provisions must be included for the collection of urine. Urinals for bed use are available for both men and women. However, for use with the present invention, some modification must be made. FIG. 7 illustrates a male urinal accessory adapted to the special environment of the present invention. The ordinarily skilled mechanic in the art will readily see which modifications and principals also relate to female urinal systems and to colostomy apparatus.

Turning to FIG. 7, the urine collection system is a tubular 33 portion terminating at the distal end in a tube communicating with a collection sump 35. The proximal end has a ring of semi-ridged material 36 which is placed behind a holding means to hold the collector against the body. The holding means shown is a an underwear type garment 37 with a hole 38 strategically placed to receive the ring and position the collection tube over the male urinary organ. The holding means may equally be the garment shown, a belt, or the air-permeable layer garment previously described. The collection tube 33 is intended to touch the skin of the wearer, thus it must be constructed of hypo-allergenic, low toxicity material to tolerate long contact.

The invention differs from prior art in that the securing portions are comprised of a launderable garment, and the collection portions are removable and either disposable or sterilizable. Furthermore, the system is designed to work submerged in water where the forces of gravity are balanced by hydrostatic forces. Prior art devices would not adequately drain the urine into the usual flexible collection bags. In the present Invention, the rigid or semi-rigidness of the collection reservoir in co-operation with specifically designed venting, allows the urine to collect. Furthermore, the urine can be withdrawn by pumping if needed.

The collection tube may be constructed of semi-ridged material, or flexible material. Flexible material requires a means to keep a passage open to the drain tube. FIG. 7 illustrates a helical shaped frame 40 near the distal end of a flaccid collection tube to resists collapse due to external water pressure. A frame as illustrated also makes a small temporary urine collection pocket. Alternate means to prevent collapse and subsequent stoppage of urine would be any mechanism that holds the walls apart providing a drain channel. Such would be bundles of fibers such as cotton or man-made fiber, common braided plastic rope, sections of tubing, and the like.

Urine collected in the collection tube is transported to a retention sump 35 which must be able to withstand the pressure of the water in the tank. FIG. 7 shows a ridged bottle type reservoir fitted with a vent tube to the atmosphere 39. A flaccid reservoir such as a common standard urine collection bag will be collapsed by the pressure and will not receive urine. To use a flaccid bag, it must have a support means to hold it open to receive urine. Suitable support is a frame similar to the collection tube previously described, a filling of a material comprising a labyrinth of interconnected voids such as a cotton batt or block of foam material, or be filled with water absorbing gel such as poly sodium acrylate capable of absorbing large quantities of liquid.

The collection sump may be located either within the suit, in the water in the tank, or outside the tank. Inside the suit eliminates the problem of a tube passing through the waterproof suit, but makes a reservoir of sufficient size more difficult to mount. Outside the suit, in the water, requires appropriate weighting to keep the sump from floating. Outside the tank permits the use and servicing of standard flaccid collection bags. The disadvantage is that a pass-through fitting must be installed in the tank side wall.

It is possible to fit a pump onto the vent tube to remove excess urine. Any pump will do. The type known as venturi ejector operates by compressed air or water, has no moving parts, valves, or lubrication, thus can be readily cleaned and sterilized.

To use the present invention in the suit embodiment, the person intending to sleep within dresses in the permeable garment, the slippery pajamas, if used, go over the permeable garment, the harness, if used, goes over the permeable garment and can be either under or over the slippery pajamas, and finally the waterproof suit having been fitted with the instrumentation and ventilating air tubes is put on, closed and sealed.

If possible, the person enters the water under his own power, otherwise appropriate help is provided using a crane and the harness if necessary.

The neck stock is closed and the comfort cushion padding 18 installed.

Any steps omitted from the above brief description are apparent from the description of the invention. Similarly, the slightly different steps to use the envelope embodiment are apparent from the description.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification and appended claims are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

I claim:

1. A buoyancy system for patient support comprising:
   a. a liquid-filled container adapted to contain a person substantially submerged therein;
   b. flexible liquid excluding envelope disposed substantially within the container, said envelope adapted to surround and contain a person, wherein the envelope has a sealed bottom and an open upper end;
   c. a supporting means for holding said open upper end open to the atmosphere and;
   d. a ventilation means comprising at least one source of compressed air, and at least one air transporting tube for transferring air from the compressed air source into the interior of the flexible envelope.

2. The system of claim 1 wherein said tube discharges air in the proximity of said sealed bottom which traverses the envelope and exits through said open end.

3. The system of claim 1 further comprising:

e. air passage means adapted for distributing air over the surface of the patient, said passage means comprising a labyrinth of air passages interposed between the interior surface of the envelope and the patient, wherein the air flows through the labyrinth of passages from said tube and exits through said open end.

4. The system of claim 1 further comprising a restraint means adapted to hold the head of the patient at said open upper end.

5. The system of claim 4, wherein said restraint means comprises a harness for supporting the head, whereby the head is adapted to rest in said harness and said harness is cooperatively attached to a trestle.

6. The system of claim 1 further comprising a restraint means adapted to hold a portion of the patient's body wherein the restraint means comprises a harness operatively attached to the body portion and cooperatively attached to a trestle.

7. The system of claim 1 further comprising a medication applying means adapted for the application of medicative material to the patient, said applying means comprising at least one tube extending from a medicament source to the interior of the envelope.

8. The system of claim 7 wherein said material is a therapeutic material selected from the group of therapeutic compounds consisting of: air, medicating gas, medicating liquid, medicating aerosol, and medicating salve.

9. The system of claim 1 further comprising a second ventilation means for removing excess medicament comprising at least one tube extending from the interior of the envelope to the exterior of the system, wherein excess medicative material is withdrawn.

10. The system of claim 3 wherein said air passage means is a fabric substantially conforming to the shape of the patient.

11. The system of claim 3 wherein said air passage means is a fabric approximately conforming to the shape of the interior of the envelope.

12. A buoyancy system for patient support comprising:

a. a liquid-filled container adapted to contain a person substantially submerged therein and;

b. a flexible liquid excluding envelope disposed substantially within the container, said envelope adapted to surround and contain a person, wherein the envelope has a sealed bottom and an open upper end and;

c. a supporting means for holding said open upper end open to the atmosphere and;

d. a ventilation means comprising at least one source of compressed air, and at least one air transporting tube for transferring air from the compressed air source into the interior of the flexible envelope and;

e. an air passage means adapted for distributing air over the surface of the patient, said passage means comprising a labyrinth of air passages interposed between the interior surface of the envelope and the patient, wherein the air flows through the labyrinth of passages from said tube and exits through said open upper end.

13. The system of claim 12 further comprising a restraint means adapted to hold the head of the patient at said open upper end.

14. The system of claim 13, wherein said restraint means comprises a harness for supporting the head, whereby the harness is adapted to hold the head in said harness and said harness is cooperatively attached to a trestle.

15. The system of claim 13 further comprising a restraint means adapted to hold a portion of the patient's body wherein the restraint means comprises a harness operatively attached to the body portion and cooperatively attached to a trestle.

16. A buoyancy system for patient support comprising:

a. a liquid-filled container adapted to contain a person substantially submerged therein, the liquid being substantially water and;

b. a flexible liquid excluding envelope disposed substantially within the container, said envelope adapted to surround and contain a person, wherein the envelope has a sealed bottom and an open upper end and;

c. a supporting means for holding said open upper end open to the atmosphere and;

d. a ventilation means comprising at least one source of compressed air, and at least one air transporting tube for transferring air from the compressed air source into the interior of the flexible envelope and;

e. an air passage means adapted for distributing air over the surface of the patient, said passage means comprising a labyrinth of air passages interposed between the interior surface of the envelope and the patient, wherein the air flows through the labyrinth of passages from said tube and exits through said open upper end and;

f. a restraint means adapted to hold the head of the patient at said open upper end.

17. The system of claim 16, wherein said restraint means comprises a harness for supporting the head, whereby the harness is adapted to hold the head in said harness and said harness is cooperatively attached to a trestle.

18. The system of claim 16 further comprising a restraint means adapted to hold a portion of the patient's body wherein the restraint means comprises a harness operatively attached to the body portion and cooperatively attached to a trestle.

19. The system of claim 16 wherein said air passage means is a fabric substantially conforming to the shape of the patient.

20. The system of claim 16 wherein said air passage means is a fabric approximately conforming to the shape of the interior of the envelope.

* * * * *